United States Patent [19]
Del Rossi et al.

[11] Patent Number: 5,461,183
[45] Date of Patent: Oct. 24, 1995

[54] REMOVAL OF ASO FROM HF/SULFOLANE ALKYLATION CATALYST

[75] Inventors: Kenneth J. Del Rossi, Woodbury; Tomas R. Melli, Sewell, both of N.J.

[73] Assignee: Mobil Oil Corporation, Fairfax, Va.

[21] Appl. No.: 272,989

[22] Filed: Jul. 15, 1994

Related U.S. Application Data

[63] Continuation-in-part of Ser. No. 117,274, Sep. 7, 1993, Pat. No. 5,382,746, which is a continuation-in-part of Ser. No. 991,918, Dec. 17, 1992, Pat. No. 5,262,579, Ser. No. 991,919, Dec. 17, 1992, Pat. No. 5,264,651, Ser. No. 991,921, Dec. 17, 1992, Pat. No. 5,264,652, and Ser. No. 991,922, Dec. 17, 1992, Pat. No. 5,276,243, said Ser. No. 991,918, Ser. No. 991,919, Ser. No. 991,921, and Ser. No. 991,922, each, is a continuation-in-part of Ser. No. 833,684, Feb. 11, 1992, Pat. No. 5,191,150.

[51] Int. Cl.$^6$ ................................ C07C 2/62; C07C 7/10
[52] U.S. Cl. .................... 585/802; 585/719; 585/723; 585/724; 585/730
[58] Field of Search ..................... 585/719, 723, 585/724, 730, 802

[56] References Cited

U.S. PATENT DOCUMENTS

| | | | |
|---|---|---|---|
| 5,262,579 | 11/1993 | Child et al. | 585/802 |
| 5,347,068 | 9/1994 | Eastman et al. | 585/724 |
| 5,382,746 | 1/1995 | Child et al. | 585/802 |
| 5,386,076 | 1/1995 | Child et al. | 585/802 |

*Primary Examiner*—Asok Pal
*Attorney, Agent, or Firm*—Alexander J. McKillop; Dennis P. Santini; Robert B. Furr, Jr.

[57] ABSTRACT

A method for separating conjunct polymers which are formed as byproducts of acid catalyzed isoparaffin-olefin alkylation and sulfolane from a mixture containing conjunct polymers, sulfolane, and hydrofluoric acid comprising stripping HF from the spent catalyst, treating the stripped, spent catalyst with hydrogen to provide a stripped hydrotreated catalyst stream, and gravitationally separating the stripped hydrotreated catalyst stream to remove conjunct polymeric byproducts.

8 Claims, 1 Drawing Sheet

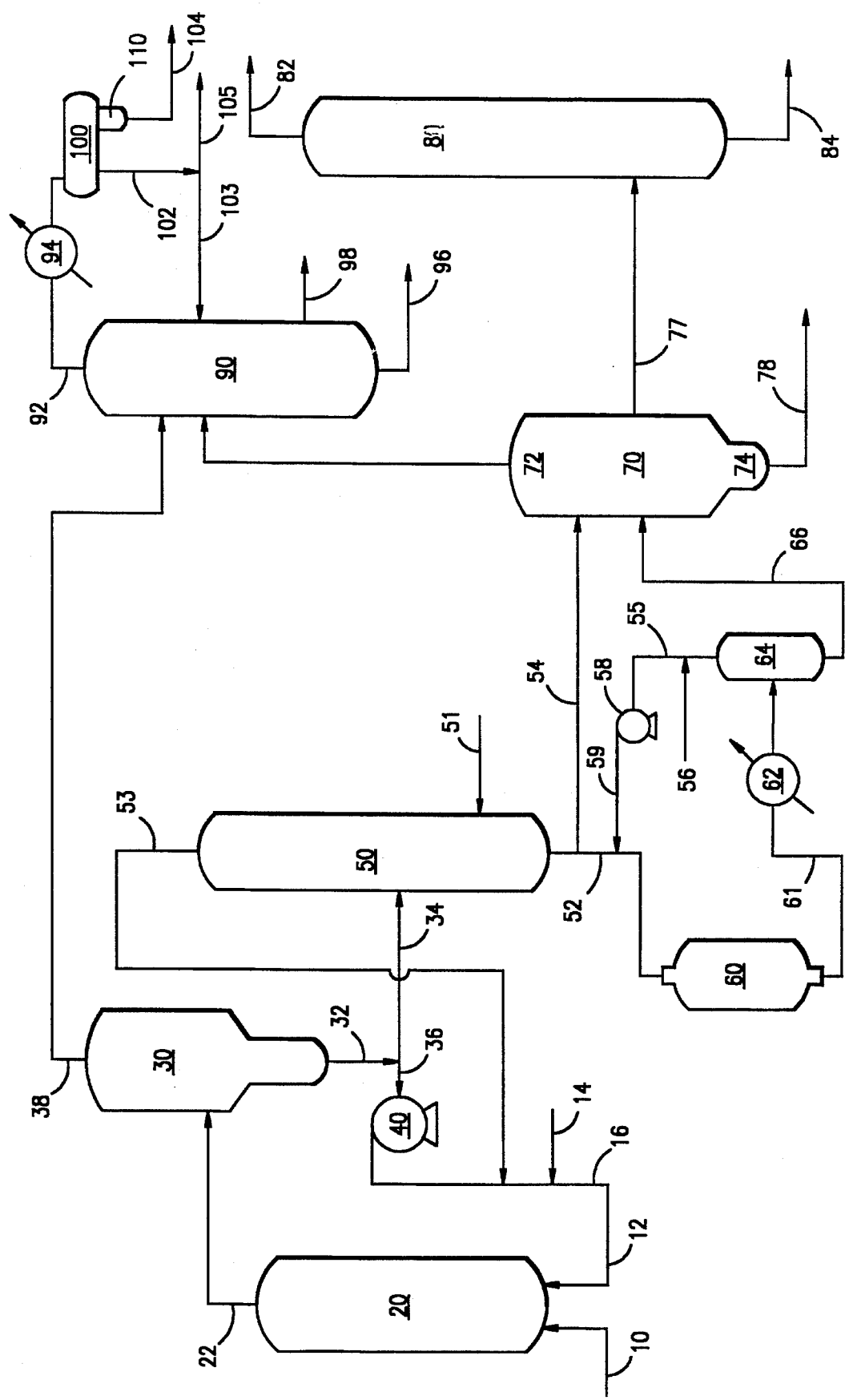

REMOVAL OF ASO FROM HF/SULFOLANE ALKYLATION CATALYST

CROSS REFERENCE TO RELATED APPLICATIONS

This is a continuation-in-part of allowed application Ser. No. 08/117,274, filed Sep. 7, 1993 (now U.S. Pat. No. 5,382,746) which is a continuation-in-part of application Ser. No. 07/991,918 (now U.S. Pat. No. 5,262,579), U.S. Ser. No. 07/991,919 (now U.S. Pat. No. 5,264,651), U.S. Ser. No. 07/991,921 (now U.S. Pat. No. 5,264,652) and U.S. Ser. No. 07/991,922 (now U.S. Pat. No. 5,276,243), all filed Dec. 17, 1992, which are continuations-in-part of application Ser. No. 07/833,684, filed Feb. 11, 1992, now U.S. Pat. No. 5,191,150.

FIELD OF THE INVENTION

The present invention relates to the art of catalytic alkylation. More specifically, the invention relates to a liquid alkylation catalyst and an isoparaffin-olefin alkylation process. Particularly, the invention provides a method of separating the sulfolane component of liquid alkylation catalyst from the conjunct polymeric byproducts evolved during catalytic isoparaffin-olefin alkylation.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry uses anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as 4,938,936 to Yan teach various methods for containing and/or neutralizing HF acid clouds following accidental releases.

But it would be particularly desirable to provide an additive which decreases the cloud forming tendency of HF without compromising its activity as an isoparaffin-olefin alkylation catalyst. Solvents and complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula R—$SO_2$—R', where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. Nos. 4,025,577 and 4,099,924 to Siskin et al. report the use of alkylation catalyst compositions containing HF, a metal halide, and sulfolane. U.S. Patent to Olah relates to an additive formulation which reduces the fuming tendency of HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The preceding references demonstrate the desirability of a liquid Bronsted acid catalyst (such as HF) for isoparaffin-olefin alkylation, as well the utility of liquid Bronsted acids in combination with metal halides, particularly metal fluorides.

Isoparaffin-olefin alkylation processes typically convert at least a portion of the feedstock to conjunct polymeric byproducts, which are more commonly referred to as acid soluble oil or ASO. While adding sulfolane to HF for isoparaffin-olefin alkylation successfully decreases the cloud-forming tendency of the mixture, it unfortunately complicates the problem of removing ASO from the system because the typical boiling range of the ASO brackets the boiling point of sulfolane (285° C., 545° F.). Thus sulfolane cannot be readily separated from ASO by distillation.

U.S. Pat. Nos. 5,191,150, 5,262,579, 5,264,650, 5,264, 651, 5,264,652, 5,264,653 and 5,304,522 teach sulfolane recovery methods which involve reducing the HF concentration in a mixture of HF, sulfolane, and ASO to less than about 30 weight percent and then gravitationally separating the resulting mixture to recover sulfolane. These U.S. Patents are incorporated herein by reference for descriptions of such catalysts and isoparaffin-olefin alkylation processes. The HF-enriched stream evolved from the stripping step of these processes contains a minor amount of relatively low boiling range conjunct polymeric byproducts (also referred to as "light acid soluble oil" or "light ASO") which is recycled to the alkylation reaction zone.

Controlling ASO concentration at low levels in the alkylation reaction zone has been found to improve isoparaffin-olefin alkylation in the presence of HF and sulfolane. Thus it would be desirable to still further improve the processes of U.S. Pat. Nos. 5,191,150, 5,262,579, 5,264,650, 5,264,651, 5,264,652, 5,264,653 and 5,304,522 by further decreasing the concentration of ASO which is present in the sulfolane recycled to the alkylation reaction zone.

SUMMARY OF THE INVENTION

The present invention provides a method for separating a mixture of HF, sulfolane, and conjunct polymeric byproducts formed in HF/sulfolane-catalyzed isoparaffin-olefin alkylation, which decreases the concentration of conjunct polymeric byproducts (ASO) recycled to the alkylation reaction zone with the recycled HF.

More particularly, the invention provides a method for separating conjunct polymers which are formed as byproducts of acid catalyzed isoparaffin-olefin alkylation and sulfolane from a mixture containing conjunct polymers, sulfolane, and hydrofluoric acid comprising the sequential steps of:

(a) alkylating an isoparaffin with an olefin in the presence of an alkylation catalyst comprising HF and sulfolane in an alkylation reaction zone in contact with at least one metal selected from Groups IB, IIB, VIB, VIIB, and VIII of the Periodic Table of the Elements, to evolve ASO byproduct and at least one compound containing a metal selected from Groups IB, IIB, VIB, VIIB, and VIII of the Periodic Table of the Elements which metal-containing compound is at least partially soluble in said alkylation catalyst;

(b) gravitationally separating effluent from said alkylation reaction zone to provide a less-dense stream containing alkylate product and unreacted isoparaffin and a more dense stream containing sulfolane, ASO, HF, and said metal-containing compound;

(c) stripping HF from said more dense stream of step (b) with isoparaffin to provide a stripper bottoms stream comprising said metal-containing compound and less than about 30 percent hydrofluoric acid by weight and a stripper overhead stream containing HF, isoparaffin, and a fraction of said ASO having a lower end boiling point than the ASO containing in said more dense stream of step (b);

(d) contacting at least a portion of said stripper bottoms stream of step (c) with hydrogen; and (e) gravitationally separating said stripper bottoms stream into a more dense sulfolane-enriched stream and a less dense stream containing saturated hydrocarbons.

The present invention may optionally further comprise the steps of:

(f) charging said stripper overhead stream to an alkylate product fractionator;

(g) recovering a product fractionator overhead stream containing isoparaffin and HF from said alkylate product fractionator; and (h) recycling said product fractionator overhead stream of step (g) to said alkylation reaction zone.

The method finds particular utility in regenerating an HF/sulfolane catalyst used in an isoparaffin-olefin alkylation process. The hydrofluoric acid concentration of the mixture is preferably decreased by stripping prior to the hydrogen treatment step. Any suitable inert stripping fluid may be employed, including normal paraffins and isoparaffins which can be charged to the stripper tower as a vapor. Isobutane and the vaporized alkylate product formed by reacting isobutane with propene and/or butene are particularly preferred stripping fluids. Two sequential stripping steps may be used, as the purity of the separated sulfolane/conjunct polymer phases improves as the hydrofluoric acid concentration decreases. If two-stage stripping is used, the enriched stripping fluid from both stripping stages is preferably charged to the product fractionator.

The effects of sequentially stripping hydrofluoric acid from the mixture before gravitational separation become particularly evident as the mixture is stripped to hydrofluoric acid levels of less than about 30 weight percent. Separation improves as the hydrofluoric acid content is decreased, with intermediate stream hydrofluoric acid concentrations preferably falling below 25 percent by weight, more preferably below about 10 percent hydrofluoric acid by weight, and most preferably below about 5 percent by weight. In a preferred embodiment, the catalyst mixture contains from about 0.5 to about 10 weight percent water.

Following the stripping step, the stripped liquid mixture is treated with hydrogen. The mixture may be treated, for example, by sparging or by countercurrent contacting within the hydrogenation reaction zone, or by directly injecting hydrogen into the stripper bottoms stream upstream from the hydrogenation reaction zone. The hydrogenation reaction zone may comprise a vessel without trays or packing, or may optionally contain inert packing. While the hydrogenation reaction zone may optionally contain a hydrogenation catalyst, the addition of a heterogeneous hydrogenation catalyst has not been found to be necessary. While not to limit the scope of the invention by a recitation of theory, it is believed that the HF/sulfolane alkylation catalyst attacks metals which are present in the alkylation reaction zone to form minor amounts of metal salts which are at least sparingly soluble in the HF/sulfolane catalyst. These salts appear to promote a hydrogenation reaction with one or more components of the stripped alkylation catalyst which markedly improves the purity of the sulfolane from the downstream gravitational separator.

| Hydrogenation Treatment Step Process Conditions | | | |
|---|---|---|---|
| | Broad | Typical | Preferred |
| Temperature, °F. | 50 to 300 | 70 to 200 | 80 to 120 |
| Pressure, psig | 50 to 500 | 75 to 250 | 100 to 150 |
| Hydrogen Dosage, SCF/Bbl | 1 to 1000 | 5 to 500 | 10 to 100 |
| WHSV, hr$^{-1}$ | 0.05 to 50 | 0.1 to 10 | 0.5 to 5 |

BRIEF DESCRIPTION OF THE DRAWINGS

The FIGURE is a simplified schematic diagram showing initial processing steps in the method of the invention.

EMBODIMENTS

Referring now to the FIGURE, mixed isoparaffin and olefin feed 10 and liquid catalyst 12 flow to riser/reactor 20. The riser/reactor effluent 22 flows to gravitational separator 30 where the effluent separates into a less dense hydrocarbon stream 38 containing alkylate and unreacted isoparaffin and a more dense catalyst stream 32 which contains essentially HF, sulfolane, water and ASO. The majority of the catalyst stream 32 recycles to riser/reactor 20 via stream 36, catalyst recycle pump 40, and stream 16. Fresh makeup HF and sulfolane enter stream 16 as required via stream 14. A minor amount of catalyst stream 32 flows to catalyst stripper 50 via stream 34. Isoparaffin (typically isobutane) from stream 51 strips HF and a lighter boiling fraction of the ASO from the catalyst mixture to produce a stripped catalyst stream 52 containing less than about 30 weight percent HF. The stripping fluid (isobutane), now enriched in HF, is recycled to line 16 and riser/reactor 20 via line 53. If the catalyst stripper overhead stream in line 53 contains a substantial amount of a lighter boiling fraction of the ASO, the stream may optionally be charged to product fractionator 90.

A portion of the stripped catalyst may be charged directly to gravitational separator 70 via line 54. Depending upon the operating temperature in catalyst stripper 50 and the relative flowrates in lines 52 and 54, line 54 may optionally flow to an in-line cooler (not shown) before charging stripped catalyst to gravitational separator 70. The relative flowrates through lines 52 and 54 may be adjusted to obtain the desired improvement in gravitational separator performance. Increasing the relative flow through line 52 (and thus decreasing the relative amount of stripped catalyst which bypasses the hydrogen treatment step) decreases the amount of ASO impurity in the sulfolane withdrawn from gravitational separator 70.

The stripped catalyst stream 52 is mixed with recycled hydrogen-rich gas 59 and charged to hyrogenation reactor 60. Make-up hydrogen is added via line 56 as required. The hydrogenation reactor may comprise any suitable vessel, and preferably contains inert packing to improve contact between the stripped catalyst and the hydrogen-rich gas. The hydrogenation reactor effluent flows through line 61 to cooler 62 and flash drum 64. Cooler 62 typically decreases the temperature of the hydrogenation reactor effluent from about 300° F. to about 70° F. before the cooled hydrogentaion reactor effluent enters flash drum 64. The liquid from flash drum 64 flows through line 66 to gravitational separator 70, while the unreacted hydrogen-rich gas together with fresh make-up hydrogen from line 56 flows through line 55 to recycle compressor 58.

Two liquid phases form within gravitational separator 70. The upper, less dense phase, enriched in hydrocarbon, collects at the top 72 of gravitational separator 70, and is withdrawn through line 76 for further processing, as described below. Solids and the most dense residual hydrocarbons collect in a bottom boot 74, and are similarly withdrawn for further processing as stream 78. The lower, more dense liquid phase, enriched in sulfolane, flows out of gravitational separator 70 as stream 77. Under normal operating conditions, sulfolane-rich stream 77 may be recycled to riser/reactor 20 without further purification. Stream 77 may optionally be further purified if operating conditions so warrant by charging stream 77 to a lower middle section of vacuum distillation tower 80 which would operate at a feed tray temperature of around 300° F. and the maximum available vacuum. Sulfolane would then flow overhead and be recycled through line 82 while higher-boiling hydrocarbon impurities would flow from the tower through line 84.

Streams 38 and 76 flow to product fractionator 90. The overhead stream 92 from product fractionator 90, enriched in isobutane and HF, condenses in overhead cooler 94 and separates into a hydrocarbon phase and an acid phase in overhead accumulator 100. The hydrocarbon phase, enriched in isobutane, leaves accumulator 100 as stream 102, and splits between reflux stream 103 and isobutane recycle stream 105. The acid phase in accumulator 100 settles in the lower boot section 110 of the accumulator and is withdrawn as stream 104 for recycle to riser/reactor 20. Alkylate product, containing a minor amount of light ASO, flows from product fractionator 90 as stream 96, while n-butane is withdrawn as side draw 98.

COMPARATIVE EXAMPLE

A mixture of about 65 weight percent hydrofluoric acid, about 30 weight percent sulfolane, and about 5 weight percent conjunct polymeric byproducts (which conjunct polymeric byproducts are evolved from the catalytic alkylation of isobutane with butene in a non-metallic vessel) is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLES 2–4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid separate more readily than mixtures having higher HF concentrations.

EXAMPLES 5–7

The composition of the Comparative Example is charged to a carbon steel vessel at a temperature of about 70° F. and pressure of about 1 atmosphere. A 10:1 wt:wt mixture of isobutane and butenes is sparged through the catalyst mixture and the hydrocarbon reactor effluent is collected. Analysis of the spent catalyst mixture shows that the spent catalyst contains approximately 0.05 weight percent soluble iron salts.

EXAMPLES 8–10

The procedure of Examples 5–7 is repeated with a 316 alloy stainless steel vessel. Analysis of the spent catalyst mixture shows that the spent catalyst contains salts of iron, chromium, and nickel which are at least partially soluble in the spent catalyst mixture.

EXAMPLES 11–13

The procedure of Examples 5–7 is repeated with a Monel brand Ni—Cu—Fe alloy vessel. Analysis of the spent catalyst mixture shows that the spent catalyst contains salts of nickel, copper, and iron which are at least partially soluble in the spent catalyst mixture.

EXAMPLES 14–16

The procedure of Examples 5–7 is repeated with a Hastelloy-C brand alloy vessel. Analysis of the spent catalyst mixture shows that the spent catalyst contains salts of nickel, chromium, iron, and tungsten which are at least partially soluble in the spent catalyst mixture.

EXAMPLES 17–19

The alkylation catalysts of Examples 2–4 are sparged with 100 scf/Bbl of hydrogen gas at 80° F. and 100 psig atmospheres pressure. The alkylation catalysts are then charged to a gravitational separator. In each case, two phases form and the purity of the sulfolane-rich phase is essentially the same as that of Examples 2–4.

EXAMPLES 20–22

The iron-containing alkylation catalysts of Examples 5–7 are sparged with 100 scf/Bbl of hydrogen gas at 80° F. and 100 psig total pressure. The alkylation catalysts are then charged to a gravitational separator. The ASO content of the sulfolane phase is lower than that of Examples 17–19.

EXAMPLES 23–25

The metals-containing alkylation catalysts of Examples 8–10 are sparged with 100 scf/Bbl of hydrogen gas at 80° F. and 100 psig total pressure. The alkylation catalysts are then charged to a gravitational separator. The ASO content of the sulfolane phase is lower than that of Examples 17–19.

EXAMPLES 26–28

The metals-containing alkylation catalysts of Examples 11–13 are sparged with 100 scf/Bbl of hydrogen gas at 80° F. and 100 psig total pressure. The alkylation catalysts are then charged to a gravitational separator. The ASO content of the sulfolane phase is lower than that of Examples 17–19.

EXAMPLES 29–31

The metals-containing alkylation catalysts of Examples 14–16 are sparged with 100 scf/Bbl of hydrogen gas at 80° F. and 100 psig total pressure. The alkylation catalysts are then charged to a gravitational separator. The ASO content of the sulfolane phase is lower than that of Examples 17–19.

Changes and modifications in the specifically described embodiments can be carried out without departing from the scope of the invention which is intended to be limited only by the scope of the appended claims.

What is claimed is:

1. A method for separating conjunct polymers which are formed as byproducts of acid catalyzed isoparaffin-olefin alkylation and sulfolane from a mixture containing conjunct polymers, sulfolane, water and hydrofluoric acid comprising the sequential steps of:

(a) alkylating an isoparaffin with an olefin in the presence of an alkylation catalyst comprising HF and sulfolane in an alkylation reaction zone in contact with at least one metal selected from Groups IB, IIB, VIB, VIIB, and VIII of the Periodic Table of the Elements, to evolve ASO byproduct and at least one compound containing a metal selected from Groups IB, IIB, VIB, VIIB, and VIII of the Periodic Table of the Elements which metal-containing compound is at least partially soluble in said alkylation catalyst;

(b) gravitationally separating effluent from said alkylation reaction zone to provide a less-dense stream containing alkylate product and unreacted isoparaffin and a more dense stream containing sulfolane, ASO, HF, and said metal-containing compound;

(c) stripping HF from said more dense stream of step (b) with isoparaffin to provide a stripper bottoms stream comprising said metal-containing compound and less than about 30 percent hydrofluoric acid by weight and a stripper overhead stream containing HF, isoparaffin, and a fraction of said ASO having a lower end boiling point than the ASO containing in said more dense stream of step (b);

(d) contacting at least a portion of said stripper bottoms stream of step (c) with hydrogen; and (e) gravitationally separating said stripper bottoms stream of step (d) into a more dense sulfolane-enriched stream and a less dense hydrocarbon-containing stream.

2. The method of claim 1 further comprising:

(f) charging said stripper overhead stream to an alkylate product fractionator;

(g) recovering a product fractionator overhead stream containing isoparaffin and HF from said alkylate product fractionator; and (h) recycling said product fractionator overhead stream of step (g) to said alkylation reaction zone.

3. The method of claim 1 wherein the isoparaffin of step (c) comprises isobutane.

4. The method of claim 1 wherein said stripping fluid comprises at least one selected from the group consisting of isobutane and normal butane.

5. The method of claim 1 wherein said stripping fluid comprises an alkylated product formed by reacting an isoparaffin with an olefin.

6. The method of claim 1 wherein said hydrofluoric acid stripping step (c) provides an intermediate stream containing less than about 30 percent hydrofluoric acid by weight.

7. The method of claim 6 wherein said hydrofluoric acid separation step provides an intermediate stream containing less than about 10 percent hydrofluoric acid by weight.

8. The method of claim 7 wherein said hydrofluoric acid separation step provides an intermediate stream containing less than about 5 percent hydrofluoric acid by weight.

* * * * *